(12) United States Patent
Goget et al.

(10) Patent No.: US 8,784,506 B2
(45) Date of Patent: Jul. 22, 2014

(54) DYE COMPOSITION HAVING A LOW CONTENT OF AMMONIA

(75) Inventors: Caroline Goget, Paris (FR); Richard Sabourin, Paris (FR); Delphine Allard, Mercier (FR); Jean-Marc Ascione, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/882,775

(22) PCT Filed: Oct. 28, 2011

(86) PCT No.: PCT/EP2011/068930
§ 371 (c)(1),
(2), (4) Date: Jun. 27, 2013

(87) PCT Pub. No.: WO2012/059410
PCT Pub. Date: May 10, 2012

(65) Prior Publication Data
US 2013/0298934 A1  Nov. 14, 2013

Related U.S. Application Data

(60) Provisional application No. 61/412,965, filed on Nov. 12, 2010.

(30) Foreign Application Priority Data

Nov. 2, 2010 (FR) ..................... 10 59014

(51) Int. Cl.
*A61Q 5/10* (2006.01)
*A61K 8/04* (2006.01)
*A61K 8/33* (2006.01)
*A61K 8/41* (2006.01)

(52) U.S. Cl.
CPC . *A61Q 5/10* (2013.01); *A61K 8/046* (2013.01); *A61K 8/33* (2013.01); *A61K 8/41* (2013.01); *A61K 8/416* (2013.01)
USPC ............................ 8/405; 8/406; 8/554; 8/111

(58) Field of Classification Search
CPC ........... A61Q 5/10; A61K 8/046; A61K 8/33; A61K 8/41; A61K 8/416
USPC ...................................... 8/405, 406, 554, 111
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Dittmar | |
| 2,375,853 A | 5/1945 | Kirby et al. | |
| 2,388,614 A | 11/1945 | Kirby et al. | |
| 2,454,547 A | 11/1948 | Bock et al. | |
| 2,961,347 A | 11/1960 | Floyd | |
| 3,206,462 A | 9/1965 | McCarty | |
| 3,227,615 A | 1/1966 | Korden | |
| 3,632,559 A | 1/1972 | Matter et al. | |
| 3,709,437 A | 1/1973 | Wright | |
| 3,874,870 A | 4/1975 | Green et al. | |
| 3,910,862 A | 10/1975 | Barabas et al. | |
| 3,912,808 A | 10/1975 | Sokol | |
| 3,917,817 A | 11/1975 | Vanlerberghe et al. | |
| 3,929,990 A | 12/1975 | Green et al. | |
| 3,937,364 A | 2/1976 | Wright | |
| 3,966,904 A | 6/1976 | Green et al. | |
| 3,986,825 A | 10/1976 | Sokol | |
| 4,001,432 A | 1/1977 | Green et al. | |
| 4,003,699 A | 1/1977 | Rose et al. | |
| 4,005,193 A | 1/1977 | Green et al. | |
| 4,013,787 A | 3/1977 | Varlerberghe et al. | |
| 4,022,351 A | 5/1977 | Wright | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,008 A | 5/1977 | Sokol | |
| 4,027,020 A | 5/1977 | Green et al. | |

(Continued)

FOREIGN PATENT DOCUMENTS

| DE | 23 59 399 | 6/1975 |
|---|---|---|
| DE | 38 43 892 | 6/1990 |

(Continued)

OTHER PUBLICATIONS

International Search Report for PCT/EP2011/068930.
PCT/IB/308 Form for PCT/EP2011/068930.
Database GNPD [Online] Mintel; Nov. 2010, "Permanent Colour Foam Colour," XP002645450, Database accession No. 1418683 (the whole document).
Henkel: "Perfect Mousse: Swarzkopfs erste dauerhafte Schaumcoloration," Sep. 2, 2010, XP002645451, Retrieved form the Internet: URL:http://www.henkel.de/presse/presse-informationen-2010__20100902-perfect-mouse-schwarzkopfs-dauerhafte-schaumcoloration-33056.htm [retrieved on Jun. 24, 2011] (the whole document).

(Continued)

*Primary Examiner* — Eisa Elhilo
(74) *Attorney, Agent, or Firm* — The Marbury Law Group, PLLC

(57) ABSTRACT

The present invention relates to a composition for dyeing human keratin fibers such as the hair, comprising: (a) one or more amphoteric surfactants at a concentration of at least 0.5% by weight relative to the total weight of the composition; (b) one or more organic alkaline agents; (c) one or more oxidizing agents; (d) one or more oxidation dye precursors; (e) an amount of ammonia of less than 1.5% by weight relative to the total weight of the composition; (f) one or more cationic polymers. The invention also relates to a process for treating human keratin fibers using this composition, and aerosol or nonaerosol devices that make it possible to apply this composition in foam form.

19 Claims, No Drawings

(56) References Cited

U.S. PATENT DOCUMENTS

| | | | |
|---|---|---|---|
| 4,031,307 | A | 6/1977 | DeMartino et al. |
| 4,075,136 | A | 2/1978 | Schaper |
| 4,131,576 | A | 12/1978 | Iovine et al. |
| 4,137,180 | A | 1/1979 | Naik et al. |
| 4,147,306 | A | 4/1979 | Bennett |
| 4,157,388 | A | 6/1979 | Christiansen |
| 4,165,367 | A | 8/1979 | Chakrabarti |
| 4,172,887 | A | 10/1979 | Vanlerberghe et al. |
| RE30,199 | E | 1/1980 | Rose et al. |
| 4,184,615 | A | 1/1980 | Wright |
| 4,189,468 | A | 2/1980 | Vanlerberghe et al. |
| 4,217,914 | A | 8/1980 | Jacquet et al. |
| 4,223,009 | A | 9/1980 | Chakrabarti |
| 4,240,450 | A | 12/1980 | Grollier et al. |
| 4,277,581 | A | 7/1981 | Vanlerberghe et al. |
| 4,348,202 | A | 9/1982 | Grollier et al. |
| 4,349,532 | A | 9/1982 | Vanlerberghe et al. |
| 4,381,919 | A | 5/1983 | Jacquet et al. |
| 4,422,853 | A | 12/1983 | Jacquet et al. |
| 4,445,521 | A | 5/1984 | Grollier et al. |
| 4,579,732 | A | 4/1986 | Grollier et al. |
| 4,591,610 | A | 5/1986 | Grollier |
| 4,598,862 | A | 7/1986 | Rice |
| 4,608,250 | A | 8/1986 | Jacquet et al. |
| 4,615,467 | A | 10/1986 | Grogan et al. |
| 4,702,906 | A | 10/1987 | Jacquet et al. |
| 4,719,099 | A | 1/1988 | Grollier et al. |
| 4,719,282 | A | 1/1988 | Nadolsky et al. |
| 4,761,273 | A | 8/1988 | Grollier et al. |
| 4,777,040 | A | 10/1988 | Grollier et al. |
| 4,839,166 | A | 6/1989 | Grollier et al. |
| 4,874,554 | A | 10/1989 | Lange et al. |
| 4,948,579 | A | 8/1990 | Jacquet et al. |
| 4,996,059 | A | 2/1991 | Grollier et al. |
| 5,009,880 | A | 4/1991 | Grollier et al. |
| 5,061,289 | A | 10/1991 | Clausen et al. |
| 5,089,252 | A | 2/1992 | Grollier et al. |
| 5,364,031 | A | 11/1994 | Taniguchi et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,766,576 | A | 6/1998 | Lowe et al. |
| 5,958,392 | A | 9/1999 | Grollier et al. |
| 6,099,592 | A | 8/2000 | Vidal et al. |
| 6,284,003 | B1 | 9/2001 | Rose et al. |
| 6,338,741 | B1 | 1/2002 | Vidal et al. |
| 6,645,258 | B2 | 11/2003 | Vidal et al. |
| 6,730,789 | B1 | 5/2004 | Birault et al. |
| 7,901,464 | B2 | 3/2011 | Hercouet et al. |
| 2002/0050013 | A1 | 5/2002 | Vidal et al. |
| 2003/0019051 | A9 | 1/2003 | Vidal et al. |
| 2004/0103488 | A1 | 6/2004 | Yamashita et al. |
| 2004/0237218 | A1* | 12/2004 | Marsh et al. ............ 8/405 |
| 2009/0191142 | A1 | 7/2009 | Hercouet et al. |
| 2011/0135591 | A1 | 6/2011 | Mueller et al. |

FOREIGN PATENT DOCUMENTS

| | | |
|---|---|---|
| DE | 41 33 957 | 4/1993 |
| DE | 195 43 988 | 5/1997 |
| EP | 0 080 976 | 6/1983 |
| EP | 0 122 324 | 10/1984 |
| EP | 0 337 354 | 10/1989 |
| EP | 0 770 375 | 11/1997 |
| EP | 1 728 500 | 12/2006 |
| EP | 2 072 034 | 6/2009 |
| EP | 2 204 160 | 7/2010 |
| FR | 1 583 363 | 10/1959 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| FR | 2 733 749 | 11/1996 |
| FR | 2 801 308 | 5/2001 |
| FR | 2 886 136 | 12/2006 |
| GB | 1026978 | 4/1966 |
| GB | 1153196 | 5/1969 |
| GB | 1546809 | 5/1979 |
| JP | 2-19576 | 1/1990 |
| JP | 2006-240266 | 9/2006 |
| WO | 94/08969 | 4/1994 |
| WO | 94/08970 | 4/1994 |
| WO | 96/15765 | 5/1996 |
| WO | 2010/020500 | 2/2010 |

OTHER PUBLICATIONS

Database GPND [Online\ Mintel; Oct. 1999, "Hair Colourants", XP002645475, Database accession No. 12945 (the whole document).

Database GNPD [Online] Mintel; Jul. 2010, "Shaking Whipped Hair Colour," XP002645452, Database accession No. 1390626 (the whole document).

Database GNPD [Online] Mintel; Oct. 2010, "Hair Color," XP002645453, Database accession No. 1422757 (the whole document).

* cited by examiner

DYE COMPOSITION HAVING A LOW CONTENT OF AMMONIA

This is a national stage application of PCT/EP2011/068930, filed internationally on Oct. 28, 2011, which claims priority to U.S. Provisional Application No. 61/412,965, filed on Nov. 12, 2010; as well as French Application FR 1059014, filed on Nov. 2, 2010.

The present invention relates to a composition for dyeing the hair that has a low content of ammonia.

Among the methods for dyeing human keratin fibers, such as the hair, mention may be made of oxidation dyeing or permanent dyeing. More particularly, this dyeing method uses one or more oxidation dyes, usually one or more oxidation bases optionally combined with one or more couplers.

In general, oxidation bases are chosen from ortho- or para-phenylenediamines, ortho- or para-aminophenols and heterocyclic compounds. These oxidation bases are colourless or weakly coloured compounds, which, when combined with oxidizing products, can give access to coloured species.

The shades obtained with these oxidation bases are often varied by combining them with one or more couplers, these couplers being chosen especially from aromatic meta-diamines, meta-aminophenols, meta-diphenols and certain heterocyclic compounds, such as indole compounds.

The variety of molecules used as oxidation bases and couplers allows a wide range of colours to be obtained.

Processes of permanent dyeing or semi-permanent dyeing under lightening conditions thus consist in using, along with the dye composition, an aqueous composition comprising at least one oxidizing agent, under alkaline pH conditions in the vast majority of cases. The alkaline agent conventionally used is ammonia which has a drawback linked to the odour emitted during use on the hair. Other alkaline agents, such as alkanolamines have been proposed as a replacement for ammonia. These agents make it possible to reduce the odour emitted, but they do not make it possible to obtain an effectiveness in terms of dyeing properties equivalent to those obtained with ammonia.

There is a constant need to develop compositions which would make it possible to obtain dyeing properties at least equal to those obtained with the dye compositions based on ammonia, with a much higher level of comfort during use, in particular by decreasing the degradation of the keratin fibers and by reducing the annoyances linked to the odour of the alkaline agents used, such as ammonia.

This objective and others are achieved by the present invention, one subject of which is thus a composition for dyeing human keratin fibers, such as the hair, comprising:
(a) at least one amphoteric surfactant at a concentration of at least 0.5% by weight relative to the total weight of the composition;
(b) at least one organic alkaline agent;
(c) at least one oxidizing agent;
(d) at least one oxidation dye precursor;
(e) an amount of ammonia of less than 1.5% by weight relative to the total weight of the composition;
(f) at least one cationic polymer.

The invention also relates to a process for treating human keratin fibers using this composition.

Another subject of the invention is a two-compartment device comprising, in one compartment, a composition containing at least 0.5% of at least one amphoteric surfactant, at least one oxidation dye precursor, at least one organic alkaline agent, ammonia, at least one cationic polymer and, in the other compartment, a composition containing one or more oxidizing agents, the amount of ammonia (expressed as $NH_3$) after mixing the two compositions being less than 1.5% by weight relative to the total weight of the composition resulting from the mixing operation.

The compositions of the various compartments are intended to be mixed together to give the composition according to the invention, just before application to the human keratin fibers.

Another subject of the invention is a device for dyeing keratin fibers, capable of forming a foam using the composition of the invention.

Other features and advantages of the invention will emerge more clearly on reading the description and the examples that follow.

In the text hereinbelow, unless otherwise indicated, the limits of a range of values are included in that range. The term "at least one" associated with an ingredient of the composition signifies "one or more".

The human keratin fibers treated via the process according to the invention are preferably the hair.

The amphoteric surfactants of use in the composition of the invention are surfactants known per se in the field of dyeing keratin fibers.

The amphoteric or zwitterionic surfactant(s) that can be used in the present invention may especially be optionally quaternized, secondary or tertiary aliphatic amine derivatives, in which the aliphatic group is a linear or branched chain containing from 8 to 22 carbon atoms, said amine derivatives containing at least one anionic group such as, for example, a carboxylate, sulphonate, sulphate, phosphate or phosphonate group. In particular, mention may be made of ($C_8$-$C_{20}$)alkylbetaines, sulphobetaines, ($C_8$-$C_{20}$)alkylamido($C_1$-$C_6$)alkylbetaines or ($C_8$-$C_{20}$)alkylamido($C_1$-$C_6$)alkylsulphobetaines, preferably ($C_8$-$C_{20}$)alkylamido($C_1$-$C_6$)alkylbetaines. Among the optionally quaternized, secondary or tertiary aliphatic amine derivatives that can be used, as defined above, mention may also be made of the compounds having the respective structures (I) and (II) below:

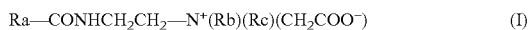

$$Ra\text{—}CONHCH_2CH_2\text{—}N^+(Rb)(Rc)(CH_2COO^-) \quad (I)$$

in which:
Ra represents a $C_{10}$-$C_{30}$ alkyl or alkenyl group derived from an acid,
Ra—COOH, preferably present in hydrolysed coconut oil, represents a heptyl, nonyl or undecyl group,
Rb represents a β-hydroxyethyl group, and
Rc represents a carboxymethyl group;
and

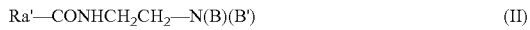

$$Ra'\text{—}CONHCH_2CH_2\text{—}N(B)(B') \quad (II)$$

in which:
B represents —$CH_2CH_2OX'$,
B' represents —$(CH_2)_z$—Y', with z=1 or 2,
X' represents the group —$CH_2$—COOH, $CH_2$—COOZ', —$CH_2CH_2$—COOH, —$CH_2CH_2$—COOZ', or a hydrogen atom,
Y' represents —COOH, —COOZ', the group —$CH_2$—CHOH—$SO_3H$ or —$CH_2$—CHOH—$SO_3Z'$,
Z' represents an ion derived from an alkali metal or alkaline-earth metal, such as sodium, an ammonium ion or an ion derived from an organic amine,
Ra' represents a $C_{10}$-$C_{30}$ alkyl or alkenyl group of an acid Ra'—COOH preferably present in hydrolysed coconut oil or in hydrolysed linseed oil, an alkyl group, especially a $C_{17}$ alkyl group, and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylampho-dipropionate, disodium caryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Among the amphoteric or zwitterionic surfactants mentioned above, use is preferably made of betaines comprising at least one saturated or unsaturated, $C_8$-$C_{30}$ fatty chain, and in particular the compounds of formula (III):

$$R_1—(CONH)_x-A_1-N^+(R_2)(R_3)-A_2-Z \quad (III)$$

with x denoting 0 or 1, $A_1$ and $A_2$ denoting, independently of one another, a linear or branched $C_1$-$C_{10}$ alkylene radical optionally substituted with a hydroxyl radical, $R_1$ denoting a linear or branched $C_6$-$C_{30}$ alkyl or alkenyl radical, $R_2$ and $R_3$ denoting, independently of one another, a linear or branched $C_1$-$C_4$ alkyl radical, Z denoting a $CO_2^-$ group or an $SO_3^-$ group.

Preferably, $R_2$ and $R_3$ denote a methyl radical.

The amphoteric surfactant(s) of betaine type used in the cosmetic composition according to the present invention may especially be ($C_8$-$C_{20}$)alkylbetaines, ($C_8$-$C_{20}$)alkylsulphobetaines, ($C_8$-$C_{20}$ alkyl)amido($C_2$-$C_8$ alkyl)betaines or ($C_8$-$C_{20}$ alkyl)amido($C_6$-$C_8$ alkyl)sulphobetaines.

Among the amphoteric surfactants mentioned above, use is preferably made of ($C_{8-20}$ alkyl)betaines and ($C_{8-20}$ alkyl)amido($C_{2-8}$ alkyl)betaines, and mixtures thereof.

More particularly, the amphoteric surfactants of betaine type ii) are selected from cocobetaine and cocamidopropylbetaine.

The composition according to the invention preferably comprises amphoteric surfactant(s) in an amount ranging from 0.5% to 30% by weight, preferably from 0.8% to 15% by weight and better still from 1% to 10% by weight, relative to the total weight of the composition.

The composition comprises at least one organic alkaline agent. Such agents are already used in cosmetics. The organic alkaline agents are preferably chosen from organic amines with a $pK_b$ at 25° C. of less than 12, preferably less than 10 and even more advantageously less than 6. It should be noted that it is the $pK_b$ corresponding to the function of highest basicity.

The organic alkaline agent(s) are chosen, for example, from alkanolamines, oxyethylenated and/or oxypropylenated ethylenediamines, amino acids and the compounds of formula (IV) below:

$$\begin{array}{c} Rx \\ \diagdown \\ N—W—N \\ \diagup \quad \diagdown \\ Ry \quad \quad Rt \end{array} \begin{array}{c} Rz \\ \diagup \end{array} \quad (IV)$$

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Alkanolamines such as monoalkanolamines, dialkanolamines or trialkanolamines comprising from one to three identical or different $C_1$-$C_4$ hydroxyalkyl radicals are in particular suitable for performing the invention.

Among compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid function chosen more particularly from carboxylic acid, sulphonic acid, phosphonic acid or phosphoric acid functions. The amino acids may be in neutral or ionic form.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (V) below:

$$R—CH_2—CH\begin{array}{c} NH_2 \\ \diagup \\ \diagdown \\ CO_2H \end{array} \quad (V)$$

in which R denotes a group chosen from:

[imidazole ring structure]
—NH—
   $—(CH_2)_2NH_2$   $—(CH_2)_2NH—C—NH_2$
                                         $\|$
                                         $NH$
   $—(CH_2)_3NH_2$   $—(CH_2)_2NHCONH_2$ The compounds corresponding to formula (V) are histidine, lysine, arginine, ornithine and citrulline.

The organic amine may also be chosen from organic amines of heterocyclic type. Besides histidine that has already been mentioned in the amino acids, mention may be made in particular of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and baleine.

The organic amine is chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulphonic acid.

According to one particular embodiment, the organic alkaline agents are chosen from alkanolamines, and/or one or more basic amino acids, preferably alkanolamines. More preferentially still, the organic amine is monoethanolamine.

The composition according to the invention generally comprises a content of organic alkaline agent(s) varying from 0.01% to 30% by weight, preferably from 0.1% to 20% by weight and better still from 1% to 10% by weight relative to the weight of said composition.

The composition according to the invention also comprises at least one oxidizing agent.

The oxidizing agents are, for example, chosen from hydrogen peroxide, urea peroxide, alkali metal bromates or ferricyanides, peroxygenated salts, for instance persulphates, perborates, peracids and precursors thereof and percarbonates of alkali metals or alkaline-earth metals. Advantageously, the oxidizing agent is hydrogen peroxide.

The content of oxidizing agent(s) more particularly represents from 0.1% to 20% by weight and preferably from 0.5% to 10% by weight relative to the weight of the composition.

As indicated previously, the composition according to the invention comprises oxidation dye precursors.

As oxidation dye precursors, use may be made of oxidation bases and couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxy-propyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-amino-phenyl)-para-phenylenediamine, N-phenyl-para-phenylenediamine, 2-β-hydroxy-ethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and their addition salts with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis-(β-hydroxyethyl)-N,N'-bis(4'-aminophenyl)-ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethyl-pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. 4,5-Diamino-1-(β-methoxyethyl)pyrazole may also be used.

A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydro-pyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo-[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo-[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one. Use is preferably made of 2,3-diamino-6,7-dihydro-1H,5H-pyrazolo[1,2-a]pyrazol-1-one and/or a salt thereof.

4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Among the couplers that may be used in the composition of the invention, mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylamino-benzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(βhydroxy-ethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]-benzimidazole, the addition salts thereof with an acid, and mixtures thereof.

The addition salts of the oxidation bases and couplers are especially chosen from the addition salts with an acid such as the hydrochlorides, hydrobromides, sulphates, citrates, succinates, tartrates, lactates, tosylates, benzenesulphonates, phosphates and acetates.

The oxidation base(s) are generally each present in an amount from 0.0001% to 10% by weight relative to the total weight of the composition, and preferably from 0.005% to 5% by weight relative to the total weight of the composition.

The coupler(s) each preferably represent from 0.0001% to 10% by weight and preferably from 0.005% to 5% by weight relative to the total weight of the composition.

The composition of the invention contains an amount of ammonia of less than 1.5%; preferably of less than 0.5%. Better still, the composition of the invention does not contain any ammonia.

The composition according to the invention may contain synthetic or natural, cationic or nonionic, dyes.

The composition of the invention comprises a cationic polymer. It is recalled that, for the purposes of the present invention, the term "cationic polymer" denotes any polymer containing cationic groups and/or groups that can be ionized into cationic groups.

Preferably, the cationic polymer present in the composition according to the invention is a linear, random, graft or block homopolymer or copolymer and comprises at least one cationic group and/or group that can be ionized into a cationic group chosen from primary, secondary, tertiary and/or quaternary amine groups that form part of the main polymer chain or that are borne by a side substituent directly connected thereto.

Advantageously, the cationic polymers that can be used in accordance with the present invention may be selected from those especially described in EP 337 354, FR 2270846, FR 2383660, FR 2598611, FR 2470596 and FR 2519863.

The cationic polymers that are preferred are chosen from those containing units comprising primary, secondary, tertiary and/or quaternary amine groups, which may either form part of the main polymer chain or be borne by a side substituent directly attached thereto.

Preferably, the cationic charge density of the cationic polymers according to the invention is greater than 1 meq/g.

This charge density is determined by the Kjeldahl method. It may also be calculated from the chemical nature of the polymer.

The cationic polymers used generally have a number-average molecular mass of between 500 and $5 \times 10^6$ approximately and preferably between $10^3$ and $3 \times 10^6$.

Among the cationic polymers, mention may more particularly be made of polymers of the polyamine, polyaminoamide and polyquaternary ammonium type.

These are known products and are especially described in patents FR 2505348 or FR 2542997. Among said polymers, mention may be made of:

(1) Homopolymers or copolymers derived from acrylic or methacrylic esters or amides and comprising at least one of the units of formula (I), (II), (III) or (IV) below:

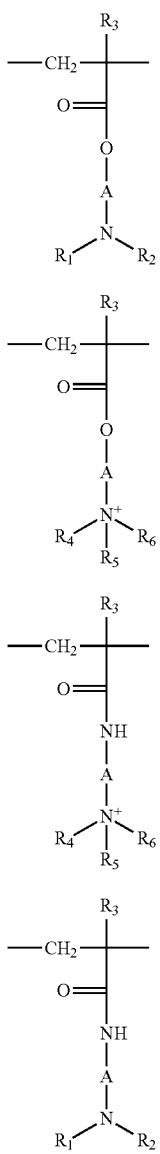

in which:

$R_3$, which may be identical or different, denote a hydrogen atom or a $CH_3$ radical;

A, which may be identical or different, represent a linear or branched $C_1$-$C_6$ and preferably $C_2$-$C_3$ alkyl group or a $C_1$-$C_4$ hydroxyalkyl group;

$R_4$, $R_5$, $R_6$, which may be identical or different, represent a $C_1$-$C_{18}$ alkyl group or a benzyl radical, and preferably a $C_1$-$C_6$ alkyl group;

$R_1$ and $R_2$, which may be identical or different, represent hydrogen or a $C_1$-$C_6$ alkyl group, and preferably methyl or ethyl;

X denotes an anion derived from a mineral or organic acid, such as a methosulphate anion or a halide such as chloride or bromide.

The polymers of family (1) can also contain one or more units derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among these polymers of family (1), mention may be made of:

copolymers of acrylamide and of dimethylaminoethyl methacrylate quaternized with dimethyl sulphate or with a dimethyl halide, such as the product sold under the name Hercofloc by the company Hercules, the copolymers of acrylamide and of methacryloyloxyethyl-trimethylammonium chloride described, for example, in EP 80 976 and sold under the name Bina Quat P 100 by the company Ciba Geigy, the copolymer of acrylamide and of methacryloyloxyethyltrimethylammonium methosulphate sold under the name Reten by the company Hercules, quaternized or non-quaternized vinylpyrrolidone/dialkylaminoalkyl acrylate or methacrylate copolymers, such as the products sold under the name Gafquat by the company ISP, for instance Gafquat 734 or Gafquat 755, or alternatively the products known as Copolymer 845, 958 and 937. These polymers are described in FR 2 077 143 and FR 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, quaternized vinylpyrrolidone/dimethylaminopropylmethacrylamide copolymers such as the product sold under the name Gafquat HS 100 by the company ISP, and the crosslinked polymers of methacryloyloxy($C_1$-$C_4$)alkyltri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, more particularly methylenebisacrylamide. Use may more particularly be made of a crosslinked acrylamide/methacryloyloxyethyltrimethylammonium chloride copolymer (20/80 by weight) in the form of a dispersion containing 50% by weight of said copolymer in mineral oil. This dispersion is sold under the name Salcare® SC 92 by the company Ciba. A crosslinked methacryloyloxyethyltrimethylammonium chloride homopolymer containing about 50% by weight of the homopolymer in mineral oil or in a liquid ester may also be used. These dispersions are sold under the names Salcare® SC 95 and Salcare® SC 96 by the company Ciba.

(2) Cationic cellulose derivatives such as cellulose copolymers or cellulose derivatives grafted with a water-soluble quaternary ammonium monomer, and disclosed in particular in U.S. Pat. No. 4,131,576, such as hydroxyalkyl celluloses, for instance hydroxymethyl, hydroxyethyl or hydroxypropyl celluloses grafted in particular with a methacryloylethyltrimethylammonium, methacrylamidopropyltrimethylammonium or dimethyldiallylammonium salt.

The commercial products corresponding to this definition are more particularly the products sold under the names Celquat L 200 and Celquat H 100 by the company National Starch.

(3) Cationic guar gums described more particularly in U.S. Pat. No. 3,589,578 and U.S. Pat. No. 4,031,307, such as guar gums containing cationic trialkylammonium groups. Use is made, for example, of guar gums modified with a 2,3-epoxypropyltrimethyl-ammonium salt (for example, chloride).

Such products are sold especially under the trade names Jaguar C13S, Jaguar C15, Jaguar C17 and Jaguar C162 by the company Meyhall.

(4) Polymers consisting of piperazinyl units and of divalent alkylene or hydroxyalkylene radicals containing straight or branched chains, optionally interrupted by oxygen, sulphur or nitrogen atoms or by aromatic or heterocyclic rings, and also the oxidation and/or quaternization products of these polymers. Such polymers are described, in particular, in FR 2 162 025 and FR 2 280 361.

(5) Water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides may be alkylated or, if they contain one or more tertiary amine functions, they may be quaternized. Such polymers are described, in particular, in FR 2 252 840 and FR 2 368 508.

Polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical is a $C_1$-$C_4$ alkyl radical and preferably denotes methyl, ethyl or propyl. Such polymers are described in particular in FR 1 583 363.

Among these derivatives, mention may be made more particularly of the adipic acid/dimethylaminohydroxypropyl/diethylenetriamine polymers sold under the name Cartaretine F, F4 or F8 by the company Sandoz.

(6) Polymers obtained by reaction of a polyalkylene polyamine containing two primary amine groups and at least one secondary amine group with a dicarboxylic acid chosen from diglycolic acid and saturated $C_3$-$C_8$ aliphatic dicarboxylic acids. The molar ratio between the polyalkylene polyamine and the dicarboxylic acid is between 0.8:1 and 1.4:1; the polyaminoamide resulting therefrom is reacted with epichlorohydrin in a molar ratio of epichlorohydrin relative to the secondary amine group of the polyaminoamide of between 0.5:1 and 1.8:1. Such polymers are described in particular in U.S. Pat. No. 3,227,615 and U.S. Pat. No. 2,961,347.

Polymers of this type are sold in particular under the name Hercosett 57, PD 170 or Delsette 101 by the company Hercules.

(7) Cyclopolymers of alkyldiallylamine or of dialkyldiallylammonium, such as the homopolymers or copolymers containing, as main constituent of the chain, units corresponding to formula (V) or (VI):

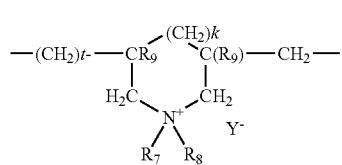

(V)

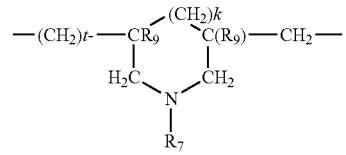

(VI)

in which formulae k and t are equal to 0 or 1, the sum k+t being equal to 1; $R_9$ denotes a hydrogen atom or a methyl radical; $R_7$ and $R_8$, independently of each other, denote a $C_1$-$C_8$ alkyl group, a hydroxyalkyl group in which the alkyl group is a $C_1$-$C_5$ alkyl group, an amidoalkyl group in which the alkyl is a $C_1$-$C_4$ alkyl group; $R_7$ and $R_8$ can also denote, together with the nitrogen atom to which they are attached, a heterocyclic group such as a piperidyl or morpholinyl group; $R_7$ and $R_8$, independently of each other, preferably denote a $C_1$-$C_4$ alkyl group; $Y^-$ is an organic or mineral anion such as bromide, chloride, acetate, borate, citrate, tartrate, bisulphate, bisulphite, sulphate or phosphate. These polymers are described in particular in FR 2 080 759 and FR 2 190 406.

The cyclopolymers comprise at least one unit of formula (V).

As regards the copolymers, they also comprise an acrylic acid or acrylamide monomer.

Among the polymers defined above, mention may be made more particularly of the dimethyldiallylammonium chloride homopolymer sold under the name Merquat 100 by the company Nalco (and its homologues of low weight-average molecular weight) and the copolymers of diallyldimethylammonium chloride and acrylamide, sold under the name Merquat 550 and the copolymers of diallyldimethyl-ammonium chloride and acrylic acid, sold in particular under the name Merquat 280.

(8) The quaternary diammonium polymer containing repeating units corresponding to the formula:

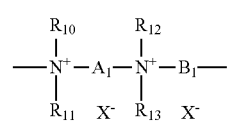

(VII)

in which formula:

$R_{10}$, $R_{11}$, $R_{12}$ and $R_{13}$, which may be identical or different, represent aliphatic, alicyclic or arylaliphatic $C_1$-$C_{20}$ radicals or hydroxyalkylaliphatic radicals, the alkyl radical of which is a $C_1$-$C_4$ alkyl radical, or alternatively $R_{10}$, $R_{11}$, $R_{12}$ and $R_{13}$, together or separately, constitute, with the nitrogen atoms to which they are attached, heterocycles optionally containing a second heteroatom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D where $R_{14}$ is an alkylene and D is a quaternary ammonium group;

$A_1$ and $B_1$ represent $C_2$-$C_{20}$ polymethylene groups which may be linear or branched, saturated or unsaturated, and which may contain, linked to or inserted in the main chain, one or more aromatic rings or one or more oxygen or sulphur atoms or sulphoxide, sulphone, disulphide, amino, alkylamino, hydroxyl, quaternary ammonium, ureido, amide or ester groups, and X⁻ denotes an anion derived from a mineral or organic acid; $A_1$, $R_{10}$ and $R_{12}$ may form, with the two nitrogen atoms to which they are attached, a piperazine ring;

moreover, if $A_1$ denotes a linear or branched, saturated or unsaturated, alkylene or hydroxyalkylene radical, $B_1$ may also denote a group $-(CH_2)_n-CO-D-OC-(CH_2)_n-$ in which n is between 1 and 100 and preferably between 1 and 50, and D denotes:

a) a glycol residue of formula: $-O-Z-O-$, where Z denotes a linear or branched hydrocarbon-based radical or a group corresponding to one of the following formulae: $-(CH_2-CH_2-O)_x-CH_2-CH_2-$; $-[CH_2-CH(CH_3)-O]_y-CH_2-CH(CH_3)-$, where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: $-NH-Y-NH-$, where Y denotes a linear or branched hydrocarbon-based radical, or alternatively the radical $-CH_2-CH_2-S-S-CH_2-CH_2-$;

d) a ureylene group of formula: $-NH-CO-NH-$.

Preferably, X⁻ is an anion such as chloride or bromide.

These polymers have a number-average molecular weight generally of between 1000 and 100 000.

Polymers of this type are described in particular in FR 2 320 330, FR 2 270 846, FR 2 316 271, FR 2 336 434, FR 2 413 907, U.S. Pat. No. 2,273,780, U.S. Pat. No. 2,375,853, U.S. Pat. No. 2,388,614, U.S. Pat. No. 2,454,547, U.S. Pat. No. 3,206,462, U.S. Pat. No. 2,261,002, U.S. Pat. No. 2,271,378, U.S. Pat. No. 3,874,870, U.S. Pat. No. 4,001,432, U.S. Pat. No. 3,929,990, U.S. Pat. No. 3,966,904, U.S. Pat. No. 4,005,193, U.S. Pat. No. 4,025,617, U.S. Pat. No. 4,025,627, U.S. Pat. No. 4,025,653, U.S. Pat. No. 4,026,945 and U.S. Pat. No. 4,027,020.

It is more particularly possible to use polymers that consist of repeating units corresponding to the following formula (VIII):

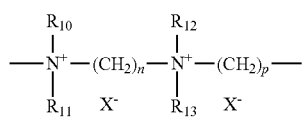

in which $R_{10}$, $R_{11}$, $R_{12}$ and $R_{13}$, which may be identical or different, denote a $C_1$-$C_4$ alkyl or hydroxyalkyl radical, n and p are integers ranging from 2 to 20 approximately, and X⁻ is an anion derived from a mineral or organic acid.

(9) Polyquaternary ammonium polymers consisting of repeating units of formula (IX):

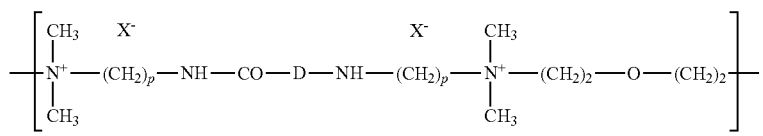

in which p denotes an integer ranging from 1 to 6 approximately, D may be nothing or may represent a group $-(CH_2)_r-CO-$ in which r denotes a number equal to 4 or 7, and X⁻ is an anion.

Such polymers may be prepared according to the processes described in U.S. Pat. No. 4,157,388, U.S. Pat. No. 4,702,906 and U.S. Pat. No. 4,719,282. They are especially described in patent application EP 122 324.

Among these polymers, examples that may be mentioned include the products Mirapol A 15, Mirapol AD1, Mirapol AZ1 and Mirapol 175 sold by the company Miranol.

(10) Quaternary polymers of vinylpyrrolidone and of vinylimidazole, for instance the products sold under the names Luviquat FC 905, FC 550 and FC 370 by the company BASF.

(11) Polyamines such as Polyquart H sold by Cognis, referred to under the name polyethylene glycol (15) tallow polyamine in the CTFA dictionary.

Other cationic polymers that may be used in the context of the invention are polyalkyleneimines, in particular polyethyleneimines, polymers containing vinylpyridine or vinylpyridinium units, condensates of polyamines and of epichlorohydrin, polyquaternary ureylenes and chitin derivatives.

Among all the cationic polymers that may be used in the context of the present invention, it is preferred to use polymers of families (1), (7), (8) and (9). In accordance with one more particular embodiment of the invention, it is preferred to use polymers of families (1), (8) and (9). According to one even more advantageous embodiment of the invention, use is made of polymers of families (8) and (9) and more preferably still of polymers having repeating units of formulae (W) and (U) below:

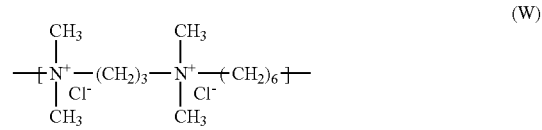

and especially those whose molecular weight, determined by gel permeation chromatography, is between 9500 and 9900;

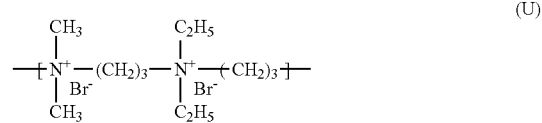

and especially those whose molecular weight, determined by gel permeation chromatography, is about 1200.

The concentration of cationic polymers in the composition according to the present invention may vary from 0.01% to 10% by weight relative to the weight of the composition, preferably from 0.05% to 6% by weight and preferably between 0.1% and 5% by weight relative to the weight of the composition.

Examples of particularly suitable direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanine direct dyes, porphyrin direct dyes and natural direct dyes, alone or as mixtures. In particular, mention may be made of direct dyes from among: azo; methine; carbonyl; azine; nitro (hetero) aryl; tri(hetero)arylmethane; porphyrin; phthalocyanine and natural direct dyes, alone or as mixtures.

When they are present, the direct dye(s) more particularly represent(s) from 0.0001% to 10% by weight and preferably from 0.005% to 5% by weight of the total weight of the composition.

The composition according to the invention may also comprise one or more additional surfactants other than amphoteric surfactants chosen from cationic, anionic or nonionic surfactants.

The term "anionic surfactant" means a surfactant comprising, as ionic or ionizable groups, only anionic groups. These anionic groups are preferably chosen from the following groups: $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2$, $HPO_2^-$, $PO_2^-$, $POH$, $PO^-$.

As examples of anionic surfactants that may be used in the composition according to the invention, mention may be made of alkyl sulphates, alkyl ether sulphates, alkylamido ether sulphates, alkylaryl polyether sulphates, monoglyceride sulphates, alkyl sulphonates, alkylamide sulphonates, alkylaryl sulphonates, alpha-olefin sulphonates, paraffin sulphonates, alkyl sulphosuccinates, alkyl ether sulphosuccinates, alkylamide sulphosuccinates, alkyl sulphoacetates, acyl sarcosinates, acyl glutamates, alkyl sulphosuccinamates, acyl isethionates and N-acyltaurates, salts of alkyl monoesters of polyglycoside-polycarboxylic acids, acyl lactylates, D-galactoside-uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds comprising from 6 to 24 carbon atoms and the aryl group denoting a phenyl group.

These compounds may be oxyethylenated and then preferably comprise from 1 to 50 ethylene oxide units.

The salts of $C_{6-24}$ alkyl monoesters of polyglycoside-polycarboxylic acids may be chosen from $C_{6-24}$ alkyl polyglycoside citrates, $C_{6-24}$ alkyl polyglycoside tartrates and $C_{6-24}$ alkyl polyglycoside sulphosuccinates.

When the anionic surfactant(s) (ii) are in salt form, it (they) may be chosen from alkali metal salts such as the sodium or potassium salt and preferably the sodium salt, the ammonium salts, the amine salts and in particular the amino alcohol salts or the alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Among the anionic surfactants, it is preferred, according to the invention, to use alkyl sulphate salts and alkyl ether sulphate salts and mixtures thereof.

The term "cationic surfactant" means a surfactant that is positively charged when it is contained in the composition according to the invention. This surfactant may bear one or more positive permanent charges or may contain one or more cationizable functions within the composition according to the invention.

The cationic surfactant(s) that may be used as conditioning agents according to the present invention are preferably selected from optionally polyoxyalkylenated primary, secondary or tertiary fatty amines, or salts thereof, quaternary ammonium salts, and mixtures thereof.

The fatty amines generally comprise at least one $C_8$-$C_{30}$ hydrocarbon-based chain. Among the fatty amines that may be used according to the invention, examples that may be mentioned include stearylamidopropyldimethylamine and distearylamine.

Examples of quaternary ammonium salts that may especially be mentioned include:

those corresponding to the general formula (VI) below:

(VI)

in which the groups $R_8$ to $R_{11}$, which may be identical or different, represent a linear or branched aliphatic group comprising from 1 to 30 carbon atoms or an aromatic group such as an aryl or an alkylaryl group, at least one of the groups $R_8$ to $R_{11}$ denoting a group containing from 8 to 30 carbon atoms and preferably from 12 to 24 carbon atoms. The aliphatic groups may comprise heteroatoms such as, in particular, oxygen, nitrogen, sulphur and halogens. The aliphatic groups are selected, for example, from $C_1$-$C_{30}$ alkyl, $C_1$-$C_{30}$ alkoxy, polyoxyalkylene ($C_2$-$C_6$), alkylamide, ($C_{12}$-$C_{22}$)alkylamido ($C_2$-$C_6$)alkyl, ($C_{12}$-$C_{22}$)alkyl acetate, and $C_1$-$C_{30}$ hydroxyalkyl groups; $X^-$ is an anion selected from the group of halides, phosphates, acetates, lactates, ($C_1$-$C_4$)alkyl sulphates, ($C_1$-$C_4$)alkyl sulphonates or ($C_1$-$C_4$)alkylaryl sulphonates.

Among the quaternary ammonium salts of formula (VI), those that are preferred are, on the one hand, tetraalkylammonium salts, for instance dialkyl-dimethylammonium or alkyltrimethylammonium salts in which the alkyl group contains approximately from 12 to 22 carbon atoms, in particular behenyltrimethyl-ammonium, distearyldimethylammonium, cetyltrimethylammonium or benzyl-dimethylstearylammonium salts, or, on the other hand, the palmitylamidopropyltrimethylammonium salt, the stearamidopropyltrimethylammonium salt, the stearamidopropyldimethylcetearylammonium salt, or the stearamidopropyl-dimethyl (myristyl acetate)ammonium salt sold under the name Ceraphyl® 70 by the company Van Dyk. It is particularly preferred to use the chloride salts of these compounds;

quaternary ammonium salts of imidazoline, such as, for example, those of formula (VII) below:

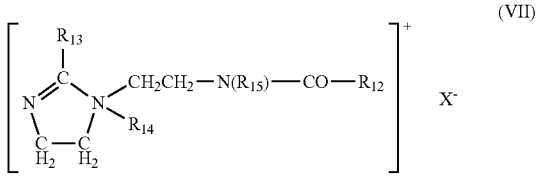
(VII)

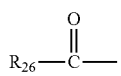

in which $R_{12}$ represents an alkenyl or alkyl group containing from 8 to 30 carbon atoms, for example tallow fatty acid derivatives, $R_{13}$ represents a hydrogen atom, a $C_1$-$C_4$ alkyl group or an alkenyl or alkyl group containing from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion selected from the group of halides, phosphates, acetates, lactates, alkyl sulphates, alkyl sulphonates or alkylaryl sulphonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, for example tallow fatty acid derivatives, $R_{14}$ denotes a methyl group, and $R_{15}$ denotes a hydrogen atom. Such a product is sold, for example, under the name Rewoquat® W 75 by the company Rewo;

quaternary diammonium or triammonium salts, in particular of formula (VIII):

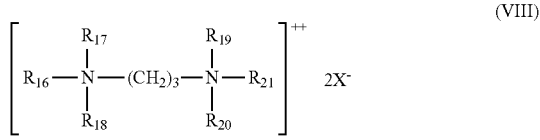
(VIII)

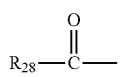

in which $R_{16}$ denotes an alkyl radical containing approximately from 16 to 30 carbon atoms, which is optionally hydroxylated and/or interrupted by one or more oxygen atoms, $R_{17}$ is selected from hydrogen or an alkyl radical containing from 1 to 4 carbon atoms or a group $(R_{16a})(R_{17a})(R_{18a})N$—$(CH_2)_3$, $R_{16a}$, $R_{17a}$, $R_{18a}$, $R_{18}$, $R_{19}$, $R_{20}$ and $R_{21}$, which are identical or different, are selected from hydrogen or an alkyl radical containing from 1 to 4 carbon atoms, and $X^-$ is an anion selected from the group of halides, acetates, phosphates, nitrates and methyl sulphates. Such compounds are, for example, Finquat CT-P, available from the company Finetex (Quaternium 89), and Finquat CT, available from the company Finetex (Quaternium 75), quaternary ammonium salts containing at least one ester function, such as those of formula (IX) below:

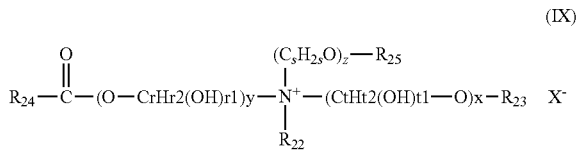
(IX)

in which:

$R_{22}$ is chosen from $C_1$-$C_6$ alkyl and $C_1$-$C_6$ hydroxyalkyl or dihydroxyalkyl groups;

$R_{23}$ is chosen from:
the group $$R_{26}-\overset{O}{\underset{\|}{C}}-$$

groups $R_{27}$, which are linear or branched, saturated or unsaturated $C_1$-$C_{22}$ hydrocarbon-based groups,
a hydrogen atom,
$R_{25}$ is chosen from:
the group $$R_{28}-\overset{O}{\underset{\|}{C}}-$$

groups $R_{29}$, which are linear or branched, saturated or unsaturated $C_1$-$C_6$ hydrocarbon-based groups,
a hydrogen atom,
$R_{24}$, $R_{26}$ and $R_{28}$, which may be identical or different, are chosen from linear or branched, saturated or unsaturated $C_7$-$C_{21}$ hydrocarbon-based groups;
r, s and t, which may be identical or different, are integers ranging from 2 to 6;
r1 and t1, which may be identical or different, are equal to 0 or 1,
and r2+r1=2r and t1+t2=2t,
y is an integer ranging from 1 to 10;
x and z, which may be identical or different, are integers ranging from 0 to 10;
$X^-$ is a simple or complex, organic or inorganic anion,
with the proviso that the sum x+y+z is from 1 to 15, that when x is 0, then $R_{23}$ denotes $R_{27}$ and that when z is 0, then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and contain from 12 to 22 carbon atoms, or may be short and contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide (chloride, bromide or iodide) or an alkyl sulphate, more particularly methyl sulphate. However, it is possible to use methanesulphonate, phosphate, nitrate, tosylate, an anion derived from an organic acid, such as acetate or lactate, or any other anion that is compatible with the ammonium containing an ester function.

The anion $X^-$ is even more particularly chloride or methyl sulphate.

Use is made more particularly in the composition according to the invention of the ammonium salts of formula (IX) in which:

$R_{22}$ denotes a methyl or ethyl group,
x and y are equal to 1;
z is equal to 0 or 1;
r, s and t are equal to 2;
$R_{23}$ is chosen from:
the group

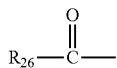

methyl, ethyl or $C_{14}$-$C_{22}$ hydrocarbon-based groups,
a hydrogen atom,
$R_{25}$ is chosen from:
the group

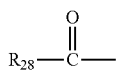

a hydrogen atom,
$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

The hydrocarbon-based groups are advantageously linear.

Mention may be made, for example, of the compounds of formula (IX) such as the diacyloxyethyldimethylammonium, diacyloxyethylhydroxyethylmethyl-ammonium, monoacyloxyethyldihydroxyethylmethylammonium, triacyloxyethylmethylammonium and monoacyloxyethylhydroxyethyldimethylammonium salts (chloride or methyl sulphate in particular), and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with $C_{10}$-$C_{30}$ fatty acids or with mixtures of $C_{10}$-$C_{30}$ fatty acids of plant or animal origin, or by transesterification of the methyl esters thereof. This esterification is followed by a quaternization using an alkylating agent such as an alkyl halide (preferably a methyl or ethyl halide), a dialkyl sulphate (preferably a dimethyl or diethyl sulphate), methyl methanesulphonate, methyl para-toluenesulphonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts.

It is also possible to use the ammonium salts containing at least one ester function that are described in U.S. Pat. No. 4,874,554 and U.S. Pat. No. 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the quaternary ammonium salts containing at least one ester function, which may be used, it is preferred to use dipalmitoylethylhydroxy-ethylmethylammonium salts.

The nonionic surfactants are more particularly chosen from monooxyalkylenated or polyoxyalkylenated, monoglycerolated or polyglycerolated nonionic surfactants. The oxyalkylene units are more particularly oxyethylene or oxypropylene units, or a combination thereof, preferably oxyethylene units.

Examples of oxyalkylenated nonionic surfactants that may be mentioned include:
 oxyalkylenated ($C_8$-$C_{24}$)alkylphenols,
 saturated or unsaturated, linear or branched, oxyalkylenated $C_8$-$C_{30}$ alcohols,
 saturated or unsaturated, linear or branched, oxyalkylenated $C_8$-$C_{30}$ amides,
 esters of saturated or unsaturated, linear or branched $C_8$-$C_{30}$ acids and of polyethylene glycols,
 polyoxyethylenated esters of saturated or unsaturated, linear or branched $C_8$-$C_{30}$ acids and of sorbitol,
 saturated or unsaturated, oxyethylenated plant oils,
 condensates of ethylene oxide and/or of propylene oxide,
  inter alia, alone or as mixtures.

The surfactants contain a number of moles of ethylene oxide and/or of propylene oxide of between 1 and 100, preferably between 2 and 50 and preferably between 2 and 30.

In accordance with one preferred embodiment of the invention, the oxyalkylenated nonionic surfactants are chosen from oxyethylenated $C_8$-$C_{30}$ alcohols comprising from 1 to 100 mol of ethylene oxide; polyoxyethylenated esters of linear or branched, saturated or unsaturated $C_8$-$C_{30}$ acids and of sorbitol comprising from 1 to 100 mol of ethylene oxide.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

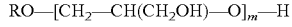

RO—[CH$_2$—CH(CH$_2$OH)—O]$_m$—H in which R represents a linear or branched $C_8$-$C_{40}$ and preferably $C_8$-$C_{30}$ alkyl or alkenyl radical, and m represents a number ranging from 1 to 30 and preferably from 1 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8$/$C_{10}$ alcohol containing 1 mol of glycerol, the $C_{10}$/$C_{12}$ alcohol containing 1 mol of glycerol and the $C_{12}$ alcohol containing 1.5 mol of glycerol.

As nonionic surfactants, mention may also be made of non-oxyethylenated fatty acid esters of sorbitan, fatty acid esters of sucrose, optionally oxyalkylenated alkylpolyglycosides, alkylglucoside esters, derivatives of N-alkylglucamine and of N-acylmethylglucamine, aldobionamides and amine oxides.

The additional surfactant(s) are preferably chosen from nonionic and anionic surfactants.

Preferably, the composition contains one or more nonionic and/or anionic surfactants.

According to one particular embodiment, the composition of the invention comprises one or more amphoteric surfactants, one or more nonionic surfactants and one or more anionic surfactants.

According to this embodiment, the nonionic surfactant is preferably chosen from oxyethylenated fatty alcohols and saturated or unsaturated, oxyethylenated plant oils. The anionic surfactant is chosen from alkyl sulphates or alkyl ether sulphates.

The total content of additional surfactants in the composition of the invention is in general from 0.1% to 30% by weight, preferably from 1% to 20% by weight and better still from 1% to 10% by weight, relative to the weight of the composition.

The total content of surfactants in the composition of the invention varies in general from 0.5% to 50% by weight and preferably from 1% to 20% by weight relative to the weight of the composition.

The composition may also contain various adjuvants conventionally used in compositions for dyeing or lightening the hair, such as anionic, cationic, nonionic polymers or mixtures thereof; antioxidants; penetrants; sequestrants; fragrances; dispersants; film-forming agents; ceramides; preserving agents; and opacifiers.

The above adjuvants are generally present in an amount for each of them of between 0.01% and 20% by weight relative to the weight of the composition.

The composition according to the invention may comprise water and/or one or more organic solvents.

Examples of organic solvents that may be mentioned include linear or branched and preferably saturated monoalcohols or diols, comprising 2 to 10 carbon atoms, such as ethyl alcohol, propyl alcohol, hexylene glycol (2-methyl-2,4-pentanediol), neopentyl glycol and 3-methyl-1,5-pentanediol, butylene glycol, dipropylene glycol and propylene glycol; aromatic alcohols such as benzyl alcohol or phenylethyl alcohol; polyols containing more than two hydroxyl functions, such as glycerol; polyol ethers, for instance ethylene glycol monomethyl, monoethyl and monobutyl ethers, propylene glycol or ethers thereof, for instance propylene glycol monomethyl ether; and also diethylene glycol alkyl ethers, especially $C_1$-$C_4$ alkyl ethers, for instance diethylene glycol monoethyl ether or monobutyl ether, alone or as a mixture.

The organic solvents, when they are present, generally represent between 1% and 40% by weight relative to the total weight of the dye composition, and preferably between 5% and 30% by weight relative to the total weight of the dye composition.

The composition is preferably aqueous. In this case it preferably comprises from 30% to 95% by weight of water, better still from 40% to 90% by weight of water, even better still from 50% to 85% by weight of water relative to the total weight of the composition.

The pH of the composition according to the invention, if it is aqueous, is generally between 3 and 12, preferably between 5 and 11 and preferentially between 7 and 11 limits included.

It may be adjusted to the desired value by means of acidifying or basifying agents usually used in the dyeing of keratin fibers, and in particular with the organic alkaline agents of the invention.

The dye composition according to the invention may be in various forms, such as in the form of liquids, creams or gels, or in any other form that is suitable for dyeing keratin fibers, and especially human hair.

Advantageously, the composition according to the invention is, on application to the keratin fibers, in the form of a foam.

The composition in foam form according to the invention is formed from a mixture of air or an inert gas with the composition described previously.

According to one particularly preferred embodiment, the composition according to the invention is in the form of a temporary foam produced just before use.

According to this embodiment, the composition may be packaged in a foam dispenser. They may either be products known as "aerosols" dispensed from a pressurized container with the aid of a propellent gas and thus forming a foam at the moment they are dispensed, or compositions dispensed from a container using a mechanical pump connected to a dispensing head, the passage of the composition into the dispensing head converting it into a foam at the latest at the outlet orifice of such a head.

According to a first variant, the dispenser may be an aerosol, containing, besides the base composition, which is generally divided into two portions, one with the oxidizing agent(s) and the other with dye precursor(s), a propellent gas. In such a configuration the two portions are generally stored separately, each in a pressurized container. Thus, the propellent gases selected in each of the containers may be suitable for the portion contained.

The propellent gas that may be used may be chosen from carbon dioxide, nitrogen, nitrogen oxide, dimethyl ether, volatile hydrocarbons such as butane, isobutane, propane, pentane, and mixtures thereof.

In practice, for this variant, use will be made of either aerosol packaging with a single container that internally contains two pouches, or a double aerosol that therefore contains two containers. In both cases, the dispensing head is such that what is sprayed in foam form is the composition according to the invention, that is to say the mixture of the composition with the oxidizing agent(s) and the composition with the oxidation dye precursor(s).

According to another embodiment, the composition may be in a foam dispenser of the "pump bottle" type. These dispensers comprise a dispensing head for delivering the composition, a pump and a dip tube for transferring the composition from the container into the head in order to deliver the product. The foam is formed by forcing the composition to pass through a material comprising a porous substance such as a sintered material, a filtering grid made of plastic or of metal, or similar structures.

Such dispensers are well known to those skilled in the art and are described in U.S. Pat. No. 3,709,437 (Wright), U.S. Pat. No. 3,937,364 (Wright), U.S. Pat. No. 4,022,351 (Wright), U.S. Pat. No. 4,147,306 (Bennett), U.S. Pat. No. 4,184,615 (Wright), U.S. Pat. No. 4,598,862 (Rice), U.S. Pat. No. 4,615,467 (Grogan et al.), and U.S. Pat. No. 5,364,031 (Tamiguchi et al.).

In practice, for this variant, the oxidizing agent(s) are packaged in a first container equipped with a closure, and the oxidation dye precursor(s) are packaged in a second container, different from the first, and also closed by a closing member. The closing member may be a pump-dispensing mechanism. The composition according to the invention is then formed by mixing, before use, a composition with the oxidizing agent(s) and a composition with the oxidation dye precursor(s). For this purpose, in order to limit the number of containers supplied, one out of the first or second container defines an internal volume large enough to receive therein the entirety of the two compositions. The mixture of the compositions may be homogenized by closing this container and by shaking the container. The closure of the container is advantageously carried out directly with the dispensing head. This dispensing head comprises a mechanical pump held in a ring intended for mounting by snap-fitting or screwing onto the neck of the container containing the mixture. The pump comprises a pump body connected to a dip tube in order to enable the whole of the mixture to be dispensed. The pump also comprises a push button for activation of the pump body, such that, on each activation, a dose of composition is sucked inside the dip tube and ejected in foam form out of the dispensing orifice of the head.

In this example, the containers are preferably made of a thermoplastic and are obtained by extrusion blow moulding or injection blow moulding processes. In particular, the container intended for packaging the composition with the oxidation dye precursor(s) is made of a material comprising a non-zero proportion of EVOH. The pump is, for example, the standard "F2-L9" model offered by the company Rexam.

According to this preferred embodiment, one subject of the invention is a non-aerosol device comprising the composition of the invention.

The dyeing process according to the invention consists in applying the composition according to the invention to wet or dry human keratin fibers over a time sufficient to develop the desired coloration. According to one embodiment, the composition applied to the keratin fibers is in foam form. The dyeing process is generally carried out at room temperature (between 15° C. and 25° C.) and up to temperatures which may reach 60° C. to 80° C.

After a leave-in time from one minute to one hour, preferably from 5 minutes to 30 minutes, the keratin fibers are rinsed with water, optionally washed with a shampoo and then rinsed with water.

The examples that follow serve to illustrate the invention without, however, being limiting in nature.

EXAMPLES

The following compositions are prepared (the amounts are expressed in g % of active material):

| Composition | weight % |
| --- | --- |
| Oxidation dye precursors (base(s) and coupler(s)) | qs shade |
| Cocobetaine | 1 |
| Sodium laureth sulphate | 1 |
| Monoethanolamine | 5 |
| Sorbitol | 4 |
| Polyquaternium-6 | 0.5 |
| Polyquaternium-39 | 0.05 |
| 40-oxyethylenated hydrogenated castor oil | 0.4 |
| Hydrogen peroxide | 4.5 |
| Glycerol | 3 |
| Cetearyl alcohol | 0.2 |
| Erythorbic acid | 0.2 |
| Sodium metabisulphite | 0.2 |
| Sodium salicylate | 0.021 |
| Tetrasodium pyrophosphate | 0.024 |
| Tetrasodium etidronate | 0.036 |
| EDTA | 0.08 |

-continued

| Composition | weight % |
| --- | --- |
| Phosphoric acid | qs pH |
| Water | qs 100 |

The composition above is obtained by mixing weight for weight, before use, two compositions A and B below:

| Composition A | weight % |
| --- | --- |
| Oxidation dye precursors (base(s) and coupler(s)) | qs shade |
| Cocobetaine | 2.5 |
| Monoethanolamine | 12.5 |
| Sorbitol | 10 |
| Polyquaternium-6 | 1.25 |
| 40-oxyethylenated hydrogenated castor oil | 1 |
| Erythorbic acid | 0.5 |
| Sodium metabisulphite | 0.5 |
| EDTA | 0.2 |
| Water | qs 100 |

| Composition B | weight % |
| --- | --- |
| Sodium laureth sulphate | 1.666 |
| Polyquaternium-39 | 0.083 |
| Hydrogen peroxide | 7.5 |
| Glycerol | 5 |
| Cetearyl alcohol | 0.333 |
| Sodium salicylate | 0.035 |
| Tetrasodium pyrophosphate | 0.04 |
| Tetrasodium etidronate | 0.06 |
| Phosphoric acid | qs pH 2.2 |
| Water | qs 100 |

The mixture is introduced in an amount of 65 g (26 g of composition A+39 g of composition B) into a pump bottle (REXAM L9 equipped with a dip tube). The device makes it possible, by pumping, to obtain a foam which is compact enough to be applied to natural or permanent-waved grey hair containing 90% white hairs and to not immediately collapse. The comfort on application is very good. After a leave-in time of 30 minutes, the locks are rinsed, washed with a standard shampoo, rinsed again and then dried, to give the desired coloration. This coloration is strong and relatively unselective.

The invention claimed is:

1. A composition for dyeing human keratin fibers, comprising:
   (a) at least one amphoteric surfactant having a concentration of at least 0.5% by weight relative to the total weight of the composition;
   (b) at least one organic alkaline agent;
   (c) at least one oxidizing agent;
   (d) at least one oxidation dye precursor;
   (e) an amount of ammonia of less than 1.5% by weight relative to the total weight of the composition; and
   (f) at least one cationic polymer.

2. The composition according to claim 1, wherein the at least one amphoteric surfactant is chosen from ($C_8$-$C_{20}$)alkylbetaines, sulphobetaines, ($C_8$-$C_{20}$)alkylamido($C_1$-$C_6$)alkylbetaines and ($C_8$-$C_{20}$)alkylamido($C_1$-$C_6$)alkylsulphobetaines.

3. The composition according to claim 1, wherein the at least one amphoteric surfactant is present in an amount ranging from 0.5% to 30% by weight, relative to the total weight of the composition.

4. The composition according to claim 1, wherein the at least one amphoteric surfactant is present in an amount ranging from 1% to 10% by weight, relative to the total weight of the composition.

5. The composition according to claim 1, wherein the at least one organic alkaline agent is chosen from organic amines with a $pK_b$ at 25° C. of less than about 12.

6. The composition according to claim 5, wherein the at least one organic alkaline agent is chosen from organic amines with a $pK_b$ at 25° C. of less than about 6.

7. The composition according to claim 1, wherein the at least one organic alkaline agent is chosen from alkanolamines.

8. The composition according to claim 1, wherein the amount of the at least one organic alkaline agent ranges from 0.01% to 30% by weight relative to the weight of the composition.

9. The composition according to claim 8, wherein the amount of the at least one organic alkaline agent ranges from 0.1% to 20% by weight relative to the weight of the composition.

10. The composition according to claim 1, wherein the at least one oxidizing agent is hydrogen peroxide.

11. The composition according to claim 1, further comprising at least one oxidation base and at least one coupler.

12. The composition according to claim 1, further comprising at least one additional surfactant chosen from cationic, anionic and nonionic surfactants.

13. The composition according to claim 1, further comprising at least one nonionic surfactant and at least one anionic surfactant.

14. The composition according to claim 1, wherein the composition does not contain ammonia.

15. The composition according to claim 1, wherein the composition is in foam form.

16. An aerosol device comprising a means of generating, in foam form, a composition for dyeing keratin fibers comprising:
  (a) at least one amphoteric surfactant having a concentration of at least 0.5% by weight relative to the total weight of the composition;
  (b) at least one organic alkaline agent;
  (c) at least one oxidizing agent;
  (d) at least one oxidation dye precursor;
  (e) an amount of ammonia of less than 1.5% by weight relative to the total weight of the composition; and
  (f) at least one cationic polymer.

17. The aerosol device according to claim 16, wherein the device comprises a single container equipped with two pouches, or wherein the device comprises two containers.

18. A nonaerosol device comprising:
  (1) a composition for dyeing keratin fibers comprising
    (a) at least one amphoteric surfactant having a concentration of at least 0.5% by weight relative to the total weight of the composition,
    (b) at least one organic alkaline agent,
    (c) at least one oxidizing agent,
    (d) at least one oxidation dye precursor,
    (e) an amount of ammonia of less than 1.5% by weight relative to the total weight of the composition, and
    (f) at least one cationic polymer;
  (2) a bottle equipped with a mechanical pumping system; and
  (3) a dispensing system enabling the composition to be delivered in foam form.

19. A process for dyeing human keratin fibers, said process comprising applying a composition comprising:
  (a) at least one amphoteric surfactant having a concentration of at least 0.5% by weight relative to the total weight of the composition,
  (b) at least one organic alkaline agent,
  (c) at least one oxidizing agent,
  (d) at least one oxidation dye precursor,
  (e) an amount of ammonia of less than 1.5% by weight relative to the total weight of the composition, and
  (f) at least one cationic polymer
to wet or dry human keratin fibers for a period of time sufficient to develop a desired coloration.

* * * * *